US009675723B2

(12) United States Patent
Chew

(10) Patent No.: US 9,675,723 B2
(45) Date of Patent: Jun. 13, 2017

(54) DEVICE AND METHOD FOR DELIVERING VOLATILE SUBSTANCES

(71) Applicant: Hydroemission Corporation Pte Ltd, Singapore (SG)

(72) Inventor: Yi Xin Chew, Singapore (SG)

(73) Assignee: HYDROEMISSION CORPORATION, PTE LTD, Singapore (SG)

( * ) Notice: Subject to any disclaimer, the term of this patent is extended or adjusted under 35 U.S.C. 154(b) by 0 days.

(21) Appl. No.: 14/767,099

(22) PCT Filed: Mar. 22, 2013

(86) PCT No.: PCT/SG2013/000115
§ 371 (c)(1),
(2) Date: Aug. 11, 2015

(87) PCT Pub. No.: WO2014/148999
PCT Pub. Date: Sep. 25, 2014

(65) Prior Publication Data
US 2015/0374871 A1    Dec. 31, 2015

(51) Int. Cl.
*A61L 9/04* (2006.01)
*A61L 9/12* (2006.01)
(Continued)

(52) U.S. Cl.
CPC ............. *A61L 9/12* (2013.01); *A01M 1/2044* (2013.01); *B32B 1/02* (2013.01); *B32B 3/06* (2013.01);
(Continued)

(58) Field of Classification Search
CPC .. A61L 9/127; A61L 9/12; A61L 9/14; A01M 1/2055; A01M 1/2044; A24F 47/002; B05B 7/2402
(Continued)

(56) References Cited

U.S. PATENT DOCUMENTS 4,502,630 A * 3/1985 Haworth ................ A61L 9/12
239/34
4,998,671 A * 3/1991 Leifheit ............. B65D 81/3261
206/219

(Continued)

FOREIGN PATENT DOCUMENTS

EP      0449271      6/1995
GB      0449271      6/1995
(Continued)

OTHER PUBLICATIONS

European Patent Office; Communication, Extended European Search Report; 7 pages.

*Primary Examiner* — Davis Hwu
(74) *Attorney, Agent, or Firm* — Renner Kenner Greive Bobak Taylor & Weber

(57) ABSTRACT

The present invention provides a device for delivering volatile substances, comprising: (i) a vapor permeable outer enclosure, said outer enclosure preferably being formed by a first laminate comprising a mesh material layer and a vapor permeable material layer laminated onto the mesh material layer; and (ii) a vapor impermeable inner enclosure placed inside the outer enclosure and defining an interior space for accommodating the volatile substances, said inner enclosure being formed by a second laminate comprising a metal foil layer and a rupturable material layer laminated onto the metal foil layer, wherein at least one die cut line to define a preformed hole is formed through the rupturable material layer. The invention also provides a method for delivering volatile substances.

20 Claims, 8 Drawing Sheets

(51) Int. Cl.
*A01M 1/20* (2006.01)
*B32B 5/14* (2006.01)
*B32B 7/14* (2006.01)
*B32B 15/08* (2006.01)
*B32B 15/20* (2006.01)
*B32B 27/32* (2006.01)
*B32B 5/02* (2006.01)
*B32B 15/085* (2006.01)
*B32B 15/088* (2006.01)
*B32B 15/09* (2006.01)
*B32B 27/12* (2006.01)
*B32B 27/34* (2006.01)
*B32B 27/36* (2006.01)
*B32B 27/40* (2006.01)
*B32B 1/02* (2006.01)
*B32B 3/06* (2006.01)
*B32B 3/26* (2006.01)
*A61M 15/08* (2006.01)

(52) U.S. Cl.
CPC ............... *B32B 3/266* (2013.01); *B32B 5/02* (2013.01); *B32B 5/145* (2013.01); *B32B 7/14* (2013.01); *B32B 15/08* (2013.01); *B32B 15/085* (2013.01); *B32B 15/088* (2013.01); *B32B 15/09* (2013.01); *B32B 15/20* (2013.01); *B32B 27/12* (2013.01); *B32B 27/32* (2013.01); *B32B 27/322* (2013.01); *B32B 27/34* (2013.01); *B32B 27/36* (2013.01); *B32B 27/40* (2013.01); *A61M 15/08* (2013.01); *B32B 2255/06* (2013.01); *B32B 2255/26* (2013.01); *B32B 2305/026* (2013.01); *B32B 2307/31* (2013.01); *B32B 2307/402* (2013.01); *B32B 2307/41* (2013.01); *B32B 2307/582* (2013.01); *B32B 2307/724* (2013.01); *B32B 2439/46* (2013.01)

(58) Field of Classification Search
USPC ..................................... 239/6, 42, 43, 47, 55
See application file for complete search history.

(56) References Cited

U.S. PATENT DOCUMENTS

| 5,458,244 | A | 10/1995 | Emori |
| 6,602,466 | B2 | 8/2003 | Hamilton et al. |
| 2002/0175105 | A1 | 11/2002 | Suzuura et al. |
| 2006/0003057 | A1 | 1/2006 | Kelly et al. |
| 2007/0138031 | A1 | 6/2007 | Miksic et al. |
| 2010/0155284 | A1 | 6/2010 | Gerstle et al. |

FOREIGN PATENT DOCUMENTS

| WO | 9712518 | 4/1997 |
| WO | WO97/12518 | 4/1997 |

* cited by examiner

DEVICE AND METHOD FOR DELIVERING VOLATILE SUBSTANCES

FIELD OF THE INVENTION

This invention relates generally to devices and methods for delivering volatiles substances, and more particularly, to a device for delivering volatile substances, which comprises an outer enclosure and an inner enclosure with at least one preformed hole for allowing the rupture of the inner enclosure to release the volatile substances, and a method for delivering volatile substances.

BACKGROUND OF THE INVENTION

A variety of volatile substances such as fragrances, essential oils, pesticides are contained in many and various forms of containers to control the release of vapor from the volatile substances for the purpose of air freshening, deodorizing, aromatherapy, air purification, air cleaning, pest repelling or pest killing. The volatile substances generally exist in the liquid or solid form.

One example of the containers in the art is of sachet type, which is made from a non-woven material (FIGS. 1 and 2). The sachet type container is not liquid proof, thus the volatile substances contained therein is limited to dry solids, otherwise the seepage or staining of the sachet material by a liquid content may occur. Usually, a porous filler material, such as sponge, foam, cork or wood, is arranged in the container to absorb the volatile substances. Since the volatile substances have to remain dry as mentioned above, the concentration of the volatile substances in the filler material is kept at low level. In some cases, the volatile substances are incorporated into a polymeric resin and injection or extrusion molded as beads, the concentration of the volatile substances are increased but remain as low as less than 50%. As a result of the low concentration of volatile substances, the treatment intensity of this type of product is very low, which means that the space to be treated is limited.

A further example of the container for the volatile substances is the type which has a vapor impermeable and rigid container 1 for the volatile substances 5 with an opening, and a membrane closure 2 firmly affixed to the opening of the container (FIGS. 3 and 4). The membrane closure 2 is provided as a single multilayer structure comprising a top layer 3 which is vapor impermeable and a bottom layer 4 which is vapor permeable. The interface between the vapor impermeable top layer and the vapor permeable bottom layer is intentionally produced with a low binding force to allow easy removal of the top layer from the bottom layer, so that the volatile substances can begin to escape when the product is to be used. The membrane type container is made from a stiff, impermeable material which can be molded into shape to form a containment area for the volatile substances and then is heat sealed to the membrane closure. The disadvantage of this container is that it is limited to shapes and designs which are flat and stiff, since the multilayer structure of the membrane enclosure cannot withstand curvature or flexing during storage as delamination of the interface between the top layer and the bottom layer may occur, leading to a premature vaporization of the volatile substances, hence shortening of the shelf life of the product. Another drawback is that the vapors can be dispensed from one side of the membrane enclosure only. The third drawback is that the membrane type product is stiff and hence cannot be inserted into narrow spaces like air vents.

The sachet type and membrane type devices are meant for use in small spaces such as cars, wardrobes and rooms. In order for imparting an air treatment effect to bigger commercial spaces such as retail stores, hotel lobbies, office buildings or shopping malls, there are machines commercially available which nebulize volatile substances into a particulate form and spray them into the air or air ducts. However, this approach requires mechanical installation, electricity and maintenance, which increases the costs of implementation.

Therefore, there is a need for a new device for delivering volatile substances which can solve the previously described drawbacks of the prior art and cater for all occasions in a simple and economic manner. Thus, the invention entails the task of creating a simple and cost-effective device that exhibits excellent storage stability and barrier properties and also provides the flexibility in all occasions including the commercial applications.

SUMMARY OF THE INVENTION

The present invention has been developed to fulfill the needs noted above and therefore has a principle object of the provision of a device for delivering volatile substances which has good barrier properties and has a reduced risk of leakage prior to use.

Another object of the invention is to provide a device for delivering volatile substances which is flexible for use in all occasions, for example, allowing insertion into narrow gaps in the air conditioning vents, commonly found in commercial spaces.

A further object of the invention is to provide a device for delivering volatile substances which is only initiated by the consumer at the time of use.

These and other objects and advantages of the invention are satisfied by providing device for delivering volatile substances, comprising:

(i) a vapor permeable outer enclosure, said outer enclosure being formed by a vapor permeable material layer; and (ii) a vapor impermeable inner enclosure placed inside the outer enclosure and defining an interior space for accommodating the volatile substances, said inner enclosure being formed by a second laminate comprising:
   a metal foil layer, and
   a rupturable material layer laminated onto the metal foil layer, wherein at least one die cut line is formed through the rupturable material layer.

Preferably, the outer enclosure is formed by a first laminate comprising a mesh material layer laminated to the vapor permeable material layer. The mesh material may be selected from a porous fabric or a porous plastic, preferably the mesh material is a material which is opaque or has a dark color, allowing the device to camouflage with, for example, the air vents where it is applied.

In one particularly preferred embodiment of the invention, the vapor permeable material is selected from a non-porous monolithic material or a microporous material whose pores are sized to allow vapor molecules to pass therethrough only. For example, the monolithic material is selected from the group consisting of polyurethane, poly(ether-co-amide), poly(ether-co-ester) and any combination thereof; and the microporous material is selected from the group consisting of polyolefins, polytetrafluoroethylenes (PTFEs), precipitated polyurethanes, and any combination thereof.

According to the invention, the mesh material layer and the vapor permeable layer may be laminated together using any suitable methods known in the art. One example of the methods is the use of adhesive which is advantageously applied in a matrix, preferably a dot matrix, so as not to cover the vapor permeable material layer completely to ensure the passage of the vapor molecules sufficiently.

In another one particularly preferred embodiment of the invention, the metal foil layer comprises or consists of aluminum foil, and the rupturable material layer comprises a polymer material, preferably a polymer laminate formed by nylon, polyester, polyolefin, or any combination thereof. For instance, the polymer laminate is formed by laminating polyethylene, nylon and polyethylene terephthalate. Other material combinations are possible for the polymer material layer, for example, the polymer material layer may be made from polyolefin only, the combination of polyester and polyolefin, or the combination of nylon and polyolefin.

As a variation of the invention, the second laminate may further comprise a heat seal lacquer layer bonded onto the metal foil layer. In this case, two sheets of the second laminate are heat-sealed along a periphery of the respective heat seal lacquer layer to form the inner enclosure.

Preferably, the die cut line defines a preformed hole. To prevent undesired or premature opening of the preformed hole, one or more points of connection may be arranged on the die cut line for linking an area of the preformed hole bound by the die cut line and the rest of the rupturable material layer. The preformed hole may be of such a configuration as square, rectangle, circle, oval shape, hexagon, octagon or the like.

The invention also relates to a method for delivering volatile substances, comprising the steps:

(a) providing a device for delivering volatile substances, comprising:
  (i) a vapor permeable outer enclosure, said outer enclosure being formed by a vapor permeable material layer; and
  (ii) a vapor impermeable inner enclosure placed inside the outer enclosure and defining an interior space for accommodating the volatile substances, said inner enclosure being formed by a second laminate comprising:
    a metal foil layer, and
    a rupturable material layer laminated onto the metal foil layer, wherein at least one die cut line which preferably defines a preformed hole is formed through the rupturable material layer; and (b) applying an external pressure through the outer enclosure, onto a region surrounding the die cut line of the inner enclosure to rupture the inner enclosure such that the volatile substances are released into the outer enclosure and are in gas or vapor communication with an ambient environment through the outer enclosure.

In comparison with the devices available in the prior art, the device for delivering volatile substances according to the invention utilizes a combination of a vapor permeable outer enclosure and a vapor impermeable inner enclosure that exhibits excellent chemical resistance and high barrier properties, thereby providing the high storage stability and ensure a long shelf life and the quality of volatile substances prior to use. The device can be initiated only after the inner enclosure is ruptured by an external force. The concentration of volatile dispensed into the ambient environment is high and pure volatile substances in liquid form can be contained in the device of the invention because of the impermeability of the inner enclosure. Further, the device of the invention is thin and flexible so that it can be applied in various air vents without interfering with the space design and layout thus becoming invisible after application.

To have a better understanding of the invention reference is made to the following detailed description of the invention and embodiments thereof in conjunction with the accompanying drawings.

BRIEF DESCRIPTION OF THE DRAWINGS

In the various figures of the drawings, like reference numbers are used to designate like parts.

DETAILED DESCRIPTION OF THE PREFERRED EMBODIMENTS

While this invention is illustrated and described in preferred embodiments, the device of the invention may be produced in many different configurations, sizes, forms and materials.

Figure 1:
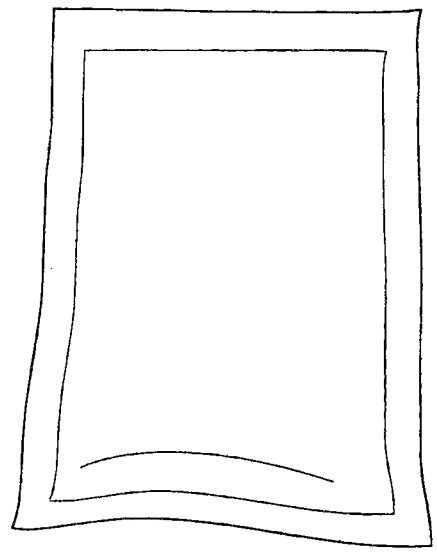
FIG. 1 is a front view of a sachet type container known in the prior art.
Figure 2:
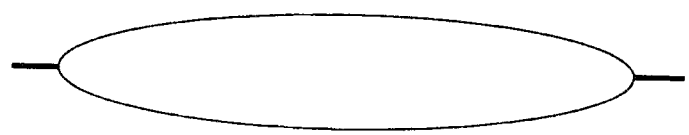
FIG. 2 is a side view of the sachet type container of FIG. 1.
Figure 3:
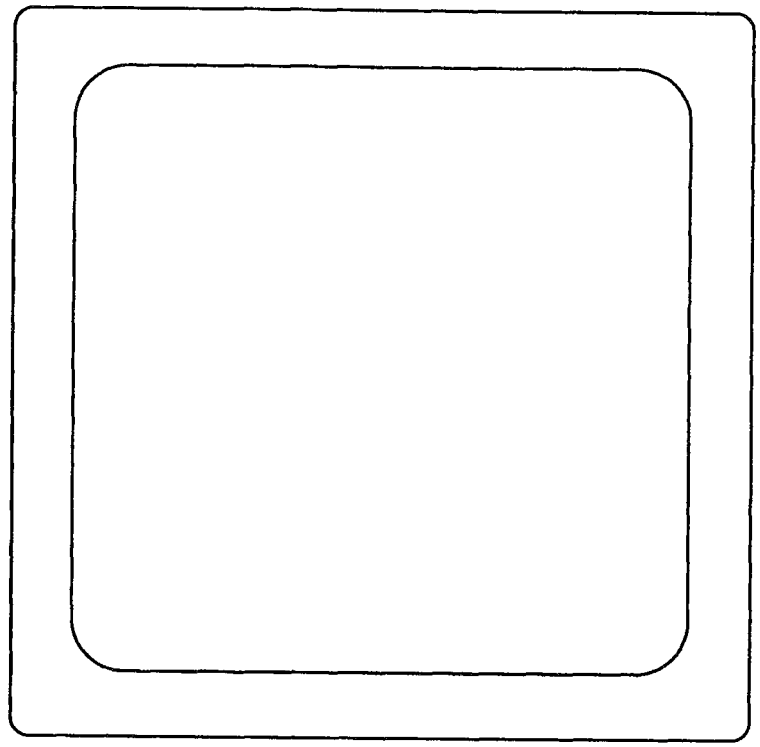
FIG. 3 is a front view of a membrane type container known in the prior art.
Figure 4:
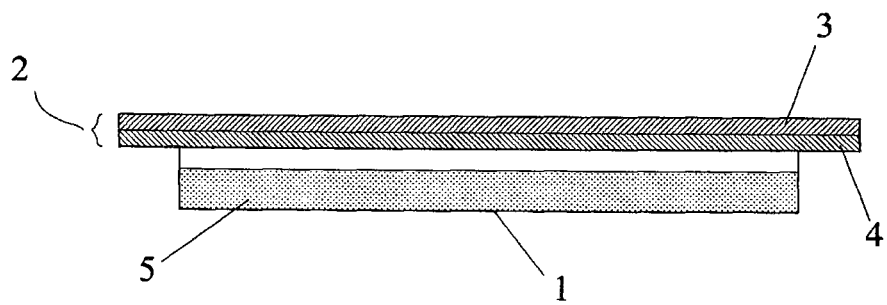
FIG. 4 is a cross sectional view of the membrane type container of FIG. 3.
Figure 5:
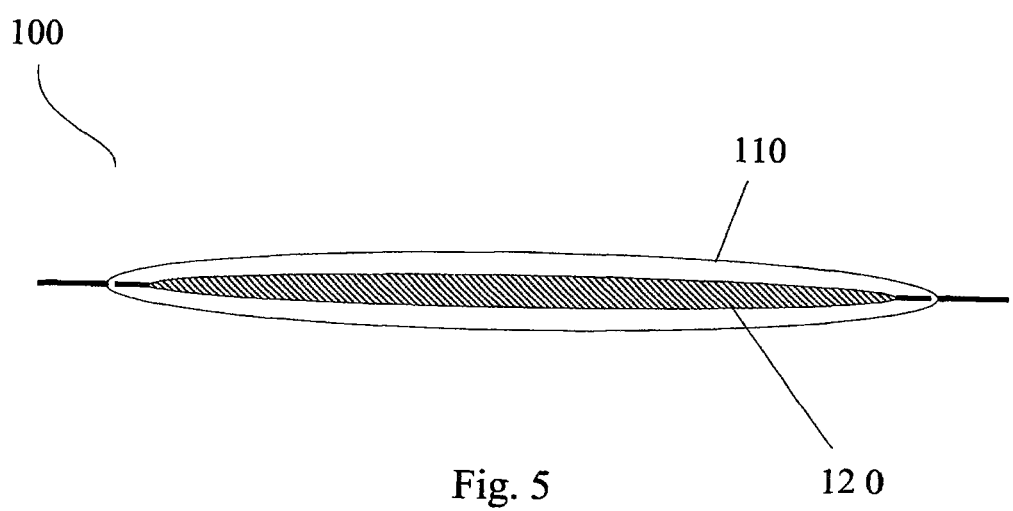
FIG. 5 is a cross sectional view of the device with the inner enclosure inside the outer enclosure.
Figure 6:
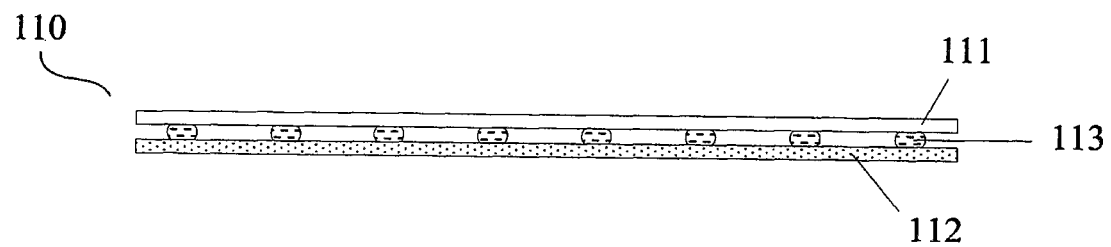
FIG. 6 is a cross sectional view of the laminar structure of an outer enclosure of a device constructed in accordance with an embodiment of the invention.

Referring now to the drawings, FIG. 5 illustratively provides a device 100 for delivering volatile substances constructed consistent with a preferred embodiment of the present invention. In this embodiment, the device 100 comprises an outer enclosure 110 and an inner enclosure 120 inside the outer enclosure 110. As illustrated, the inner enclosure 120 is fully and freely placed inside the space defined by the outer enclosure 110.

Figure 7:
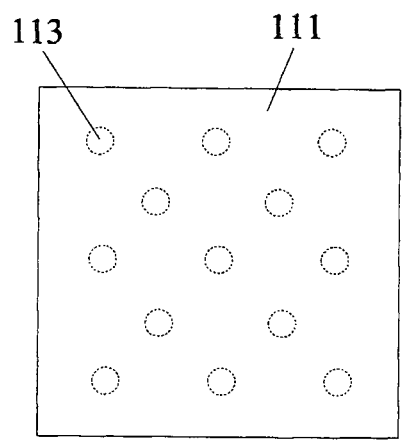
FIG. 7 is a front view of the laminar structure of FIG. 6.

FIGS. 6 to 9 illustrate the outer enclosure 110 of the device 100. In this embodiment, the outer enclosure 110 is made from a first laminate comprising a mesh material layer 111 and a vapor permeable material layer 112 bonded to the mesh material layer 111 by adhesive 113 resistant to the volatile substances. The adhesive 113 is applied in a dot matrix so as not to cover the vapor permeable material layer 112 to affect the permeability thereof, as shown in FIG. 7. It would be within the ability of a person skilled in the art that other suitable methods, for example heat bonding, may be envisioned for holding the two layers together.

The mesh material layer 111 serves as an outer layer of the outer enclosure 110 and is made from a material having small pores to allow the volatile substances to permeate into the ambient. Preferably, the mesh material is selected from a porous fabric or a porous plastic. More preferably, the opaque or dark color material is used for the purpose of acting as a colored cover to camouflage with the air vents where the device 100 is applied. The mesh material layer 111 also allows printing of logos or marketing messages thereon.

The vapor permeable material layer 112 allows the vapor molecules of the volatile substances to permeate therethrough when the volatile substances are exposed to the layer 112, and then pass through the pores of the mesh material layer 111 into the ambient. The vapor permeable material layer 112 may be made from a monolithic material or a microporous material whose pores are sized to allow vapor molecules to pass therethrough only.

The monolithic material may be selected from the group consisting of polyurethane, poly(ether-co-amide), poly(ether-co-ester) and any combination thereof. The monolithic material generally has no pores and allows vapor molecules to be transported through the material from inside to the outside by way of an absorption and evaporation process, and liquid in contact with the monolithic material cannot pass through, as discussed in US 2005/0145711A1, the disclosure of which is incorporated herein in its entirety by reference.

The microporous material used in the invention may be selected from the group consisting of polyolefins, polytetrafluoroethylenes (PTFEs), precipitated polyurethanes, and any combination thereof. They have microscopic pores that permit gas and vapor molecules to pass therethrough. Because they have such low surface energy that the surface tension of the liquid in contact with them remains too high to allow the liquid molecules to squeeze through the pores.

Put simply, the material for the vapor permeable material layer 112 is selected such that only gas and vapor molecules are able to pass therethrough but the passage of the liquid molecules are not permitted, which avoids seepage or staining.

The rational of using the laminar structure of the outer enclosure 110 is that the vapor permeable material layer 112 may swell when it comes in contact with some types of volatile substances and hence loses its shape, especially so if the monolithic materials are employed as they have lower chemical resistance compared to the microporous materials. So the mesh material layer 111 in the invention would serve, as a support for the vapor permeable material layer 112 and keep the layer 112 in shape even though it may swell.

In the case that the monolithic material is used as the vapor permeable material layer 112, it has already been found that the thinner the layer 112 is, the higher permeability of the layer 112 is achieved. The preferred thickness is about 0.015 mm to 0.03 mm for a thermoplastic polyurethane material used. However, the thin layer means that it may be fragile and soft, hence it is difficult to handle. For this purpose, the mesh material layer 111 provides the additional support and protection for the layer 112.

Figure 8:
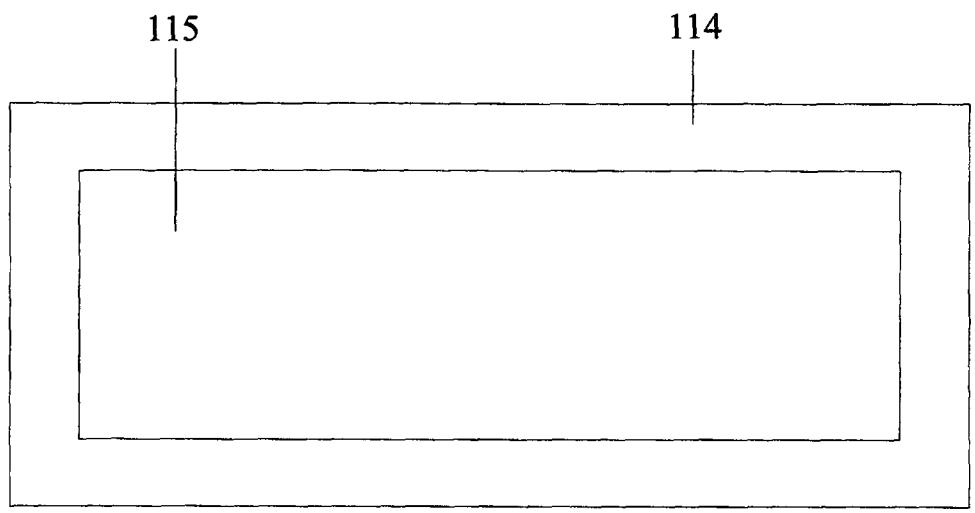
FIG. 8 is a front view of the outer enclosure having the laminar structure of FIGS. 6 and 7.
Figure 9:
FIG. 9 is a side view of the outer enclosure of FIG. 8.

In general, two sheets of the first laminate are heat-sealed along a periphery 114 of the respective vapor permeable material layer to form the outer enclosure and define a first space 115 for placement of the inner enclosure 120, as shown in FIGS. 8 and 9.

Figure 10:
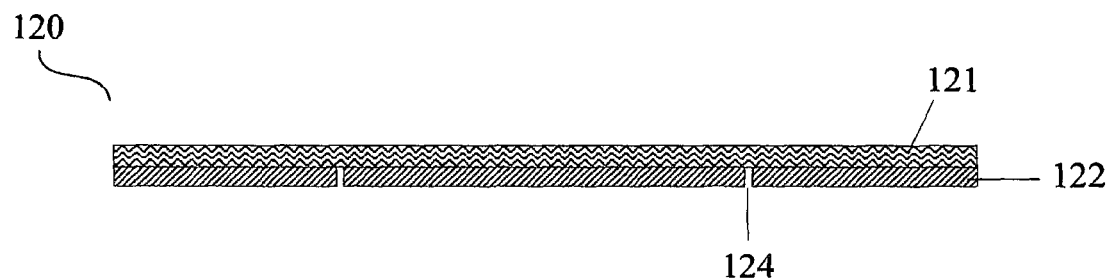
FIG. 10 is a cross sectional view of the structure of an inner enclosure of a device constructed in accordance with an embodiment of the invention, with a die cut line to define a preformed hole.
Figure 11:
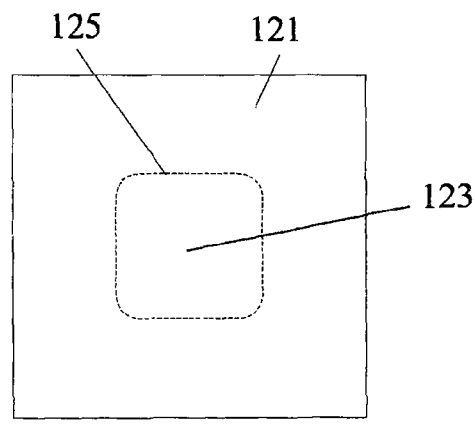
FIG. 11 is a front view of the preformed hole defined by the die cut line shown in FIG. 10.

Now turning to FIGS. 10 and 11, there is illustrated an inner enclosure 120 which is impermeable to the volatile substances constructed in accordance with one embodiment of the invention. In this embodiment, the inner enclosure 120 is formed by a second laminate comprising an aluminum foil layer 121 and a polymer material layer 122 laminated onto the aluminum foil layer 121. The polymer material layer 122 may be vapor permeable or vapor impermeable, the impermeability of the inner enclosure is provided by the aluminum foil layer 121 which is vapor impermeable.

The polymer material layer 122 is rupturable so that it may be ruptured by application of an external force. For the aggressive, corrosive or chemical volatile substances, the polymer material layer 122 is preferably chemically resistant. In the invention, the polymer material layer 122 may be made from a polymer laminate formed by nylon, polyester, polyolefin or any combinations thereof. For instance, the polymer laminate is formed by laminating polyethylene, nylon and polyethylene terephthalate as a multilayer structure.

Before the lamination of the two layers 121 and 122 takes place, the rupturable polymer material layer 122 is subject to a die-cutting process where one or more preformed holes are created to extend through the rupturable polymer material layer 122, as shown in FIG. 10. In particular, a die-cut line 124 is formed to define the preformed hole and the tear lines can be created easily and propagate along the lines 125 of weakness to create an opening. A plurality of preformed holes of various configurations may be created according to the actual needs.

Instead of a thorough cut, the rupturable polymer material layer 122 is die cut such that one or more narrow points of connection (not shown) along the die cut line 124 for linking the area bound by the die cut line 124 and the rest of layer 122. The narrow points of connection are arranged regularly along the die cut line 124.

After the die cut process is completed, the rupturable polymer material layer 122 is ready to be laminated onto the aluminum foil layer 121. Since the aluminum foil layer 121 is breakable, the area of the aluminum foil layer 121 just above the die cut line 124 of the polymer material layer 122 and covering the preformed hole becomes a line of weakness 125 which represented by dotted line in the figures. The line of weakness 125 defines an area of weakness 123. When a light pressure for example an external force is applied to the area of weakness 123, the entire portion of the weakness area of the inner enclosure 120 would be easily pushed away to create an opening, thereby rendering the volatile substances accommodated therein to be exposed to the vapor permeable material layer 112 of the outer enclosure 110. The vapor molecules of the volatile substances are therefore allowed to permeate the outer enclosure to the ambient.

In the inner enclosure as illustrated in FIGS. 10 and 11, two sheets of the second laminate are heat-sealed along a periphery 128 of the respective rupturable polymer material layer 122 to form the inner enclosure in the form of sealed pouch, with the polymer material layer 122 as an inner layer. The inner enclosure 120 defines a second space 127 for accommodating the volatile substances.

Figure 12:
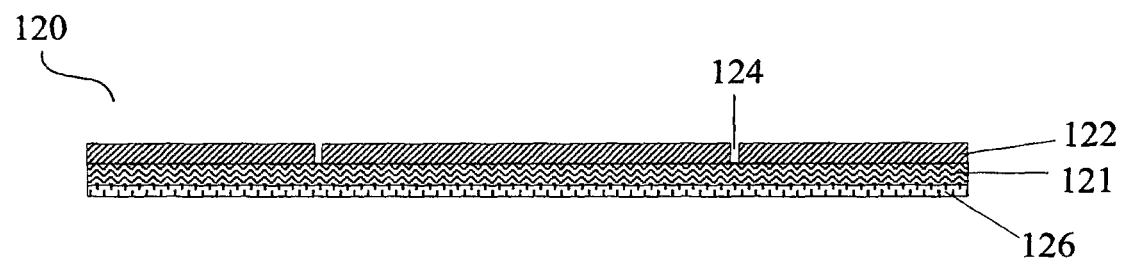
FIG. 12 is a cross sectional view of the structure of an inner enclosure of a device constructed in accordance with another embodiment of the invention, with a die cut line to define a preformed hole.
Figure 13:
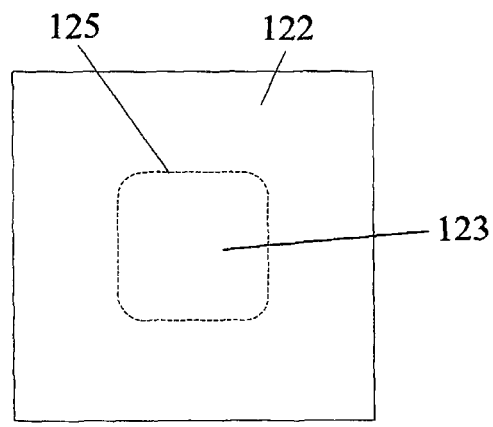
FIG. 13 is a front view of the preformed hole defined by the die cut line shown in FIG. 12.
Figure 14:
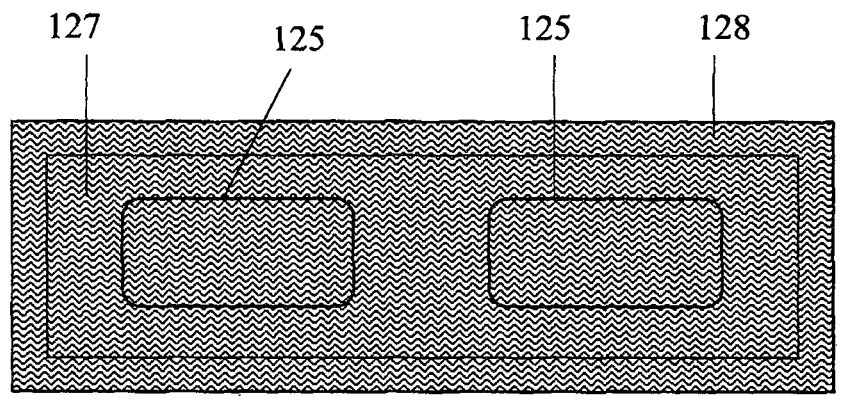
FIG. 14 is a front view of the inner enclosure having the laminar structure of FIG. 10 or 12.
Figure 15:
FIG. 15 is a side view of the outer enclosure of FIG. 14.

FIGS. 12 and 13 provide a variation of the inner enclosure 120. In this embodiment, the inner enclosure 120 further comprises a heat seal lacquer layer 126 bonded onto another side of the aluminum foil layer 121, so that the aluminum foil layer 121 is sandwiched between the rupturable polymer layer 122 and the heat seal lacquer 126. The description of the aluminum foil layer 121 and the rupturable polymer layer may be made with reference to the previous embodiment shown in FIGS. 10 and 11. In this embodiment, two sheets of the second laminate are heat-sealed along a periphery of the respective heat seal lacquer 126 to form the inner enclosure with the polymer material layer 122 as an outer layer and the heat seal lacquer 126 as an inner layer.

To initiate the device of the invention, the consumer is required to apply a light pressure onto the area of weakness of the inner enclosure 120 to rupture the inner enclosure, so as to allow exposure of the volatile substances to the outer enclosure 110. The vapors of the volatile substances would permeate from the permeable polymer material layer through the pores of the mesh material layer into the ambient.

According to the invention, the double layer structure of the outer and inner enclosures provides excellent barrier properties of the devices, as the volatile substances are contained within a complete aluminum foil layer which is completely impermeable to vapors of the volatile substances and other atmospheric agents such as oxygen, thus preventing oxidation of the volatile substances and ensuring their integrity prior to use.

The device of the invention can be made thin and flexible for use in the narrow spaces such as air vents, which cannot be achieved by the sachet products due to the solid and bulky nature of the contents or by the membrane products due to the stiff container for holding the contents.

As described above, the rupturable polymer material layer of the invention may be highly resistant to chemical components, and thus suitable for containing aggressive or chemical products, such as perfumes and air fresheners. The chemical ingredients cannot permeate the inner enclosure during transportation and storage or prior to the use of the product. This ensures the integrity of the volatile substances and the long shelf life of the product.

The invention thus provides a method and a device for delivering volatile substance which is flexible in all purposes occasions including narrow spaces like air vents, reliable and low cost to manufacture. The opaque and colored mesh material layer makes it invisible, so that the ambient design and layout would not be affected by the device of the invention.

While the embodiments described herein are intended as an exemplary device for delivering volatile substances, it will be appreciated by those skilled in the art that the present invention is not limited to the embodiments illustrated. Those skilled in the art will envision many other possible variations and modifications by means of the skilled person's common knowledge without departing from the scope of the invention, however, such variations and modifications should fall into the scope of this invention.

What is claimed is:

1. A device for delivering volatile substances, comprising:
   (i) a vapor permeable outer enclosure, said outer enclosure being formed by a vapor permeable material layer; and
   (ii) a vapor impermeable inner enclosure placed inside the outer enclosure and defining an interior space for accommodating the volatile substances, said inner enclosure being formed by a second laminate comprising:
      a metal foil layer, and
      a rupturable material layer laminated onto the metal foil layer, wherein at least one die cut line is formed through the rupturable material layer such that the material layer, when ruptured, is ruptured along the at least one die cut line.

2. The device as claimed in claim 1, wherein the outer enclosure is formed by a first laminate comprising a mesh material layer laminated to the vapor permeable material layer.

3. The device as claimed in claim 2, wherein two sheets of the first laminate are heat-sealed along a periphery of the respective vapor permeable material layer to form the outer enclosure.

4. The device as claimed in claim 1, wherein the metal foil layer comprises or consists of aluminum foil.

5. The device as claimed in claim 1, wherein the second laminate further comprises a heat seal lacquer layer bonded onto the metal foil layer.

6. The device as claimed in claim 1, wherein the rupturable material layer is a polymer material.

7. The device as claimed in claim 6, wherein the polymer laminate is formed by laminating polyethylene, nylon and polyethylene terephthalate.

8. The device as claimed in claim 1, wherein two sheets of the second laminate are heat-sealed along a periphery of the respective rupturable material layer to form the inner enclosure.

9. The device as claimed in claim 1, wherein the die cut line defines a preformed hole.

10. The device as claimed in claim 9, wherein one or more points of connection are arranged on the die cut line for linking an area of the preformed hole bound by the die cut line and the rest of the rupturable material layer.

11. The device as claimed in claim 1, wherein the outer and inner enclosures are provided in the form of a sealed pouch.

12. A method for delivering volatile substances, comprising the steps:
   (a) providing a device for delivering volatile substances, comprising:
      (i) a vapor permeable outer enclosure, said outer enclosure being formed by a vapor permeable material layer; and
      (ii) a vapor impermeable inner enclosure placed inside the outer enclosure and defining an interior space for accommodating the volatile substances, said inner enclosure being formed by a second laminate comprising:
         a metal foil layer, and
         a rupturable material layer laminated onto the metal foil layer, wherein at least one die cut line is formed through the rupturable material layer such that the material layer, when ruptured, is ruptured along the at least one die cut line; and
   (b) applying an external pressure onto a region surrounding the die cut line of the inner enclosure to rupture the inner enclosure such that the volatile substances are released into the outer enclosure and are in gas or vapor communication with an ambient environment through the outer enclosure.

13. The method as claimed in 12, wherein the second laminate further comprises a heat seal lacquer layer bonded onto the metal foil layer.

14. The method as claimed in claim 12, wherein the outer enclosure is formed by a first laminate comprising a mesh material layer laminated to the vapor permeable material layer.

15. The method as claimed in claim 12 or 13, wherein the rupturable material layer is a polymer material, preferably a polymer laminate formed by nylon, polyester, polyolefin, or any combination thereof.

16. The method as claimed in claim 15, wherein the polymer laminate is formed by laminating polyethylene, nylon and polyethylene terephthalate.

17. The method as claimed in claim 12, wherein the die cut line defines a preformed hole on the inner enclosure, and the external pressure is applied onto the preformed hole.

18. The method as claimed in claim 17, wherein one or more points of connection are arranged on the die cut line for linking an area of the preformed hole bound by the die cut line and the rest of the rupturable material layer.

19. The device as claimed in claim 1, wherein the polymer material is a polymer laminate formed by nylon, polyester, polyolefin, or any combination thereof.

20. The method as claimed in claim 15, wherein the polymer material is a polymer laminate formed by nylon, polyester, polyolefin, or any combination thereof.

* * * * *